United States Patent [19]

Leckrone et al.

[11] Patent Number: 5,026,367
[45] Date of Patent: Jun. 25, 1991

[54] LASER ANGIOPLASTY CATHETER AND A METHOD FOR USE THEREOF

[75] Inventors: Michael E. Leckrone; Jonathan Kagan; Darryl A. Knight; Larry A. Gunseor, all of Indianapolis, Ind.

[73] Assignee: Cardiovascular Laser Systems, Inc., Indianapolis, Ind.

[21] Appl. No.: 169,937

[22] Filed: Mar. 18, 1988

[51] Int. Cl.$^5$ .............................................. A61B 17/36
[52] U.S. Cl. ........................................ 606/7; 604/21; 604/101; 128/398
[58] Field of Search ............... 604/20, 21, 101; 128/4, 128/6, 303.1, 303.11, 395-398; 606/7, 14-17

[56] References Cited

U.S. PATENT DOCUMENTS

| | | | |
|---|---|---|---|
| 3,850,162 | 11/1974 | Iglesias | 128/6 |
| 4,072,147 | 2/1978 | Hett | 128/395 |
| 4,207,874 | 6/1980 | Choy | 604/21 |
| 4,418,688 | 12/1983 | Loeb | 128/303.1 |
| 4,445,892 | 5/1984 | Hussein et al. | 128/4 |
| 4,576,177 | 3/1986 | Webster, Jr. | 128/303.1 |
| 4,597,380 | 7/1986 | Raff et al. | 128/395 |
| 4,627,436 | 12/1986 | Leckrone | 128/398 |
| 4,741,327 | 5/1988 | Yabe | 128/6 |
| 4,747,045 | 5/1988 | Leckrone | 128/398 |
| 4,760,840 | 8/1988 | Fournier, Jr. et al. | 128/303.1 |
| 4,770,653 | 9/1988 | Shturman | 604/21 |
| 4,848,339 | 7/1989 | Rink et al. | 128/398 |

FOREIGN PATENT DOCUMENTS 3617019 11/1987 Fed. Rep. of Germany ... 128/303.1
8606642 11/1986 PCT Int'l Appl. ............. 128/303.1

OTHER PUBLICATIONS

Grady, "The Artery Zapper", *Discover* Dec. 1982, pp. 36-40.

Primary Examiner—Stephen C. Pellegrino
Assistant Examiner—Ralph Lewis
Attorney, Agent, or Firm—Ice Miller Donadio & Ryan

[57] ABSTRACT

The disclosure relates to a device for use in removing undesired material, e.g., an occlusion or plaque, from a duct or blood vessel within a patient's body. The device comprises a catheter adapted to be disposed within a duct and having a distal end portion with a tip and a tapered surface extending from the tip to the side of the catheter. The catheter has a lumen extending through the length thereof. The intersection of the lumen and the tapered surface forming an elongated opening: Pulsed laser energy is applied by an optical fiber extending through the lumen to the elongated openings and thereby the undesired material. An inflatable bladder is provided for positioning the distal end portion of the catheter adjacent the inner surface of the duct to position the elongated opening adjacent the undesired material to be removed. A filament extending through the catheter and connected to the distal end portion can be rotated at the proximal end of the catheter to rotatably position the distal portion thereof.

15 Claims, 5 Drawing Sheets

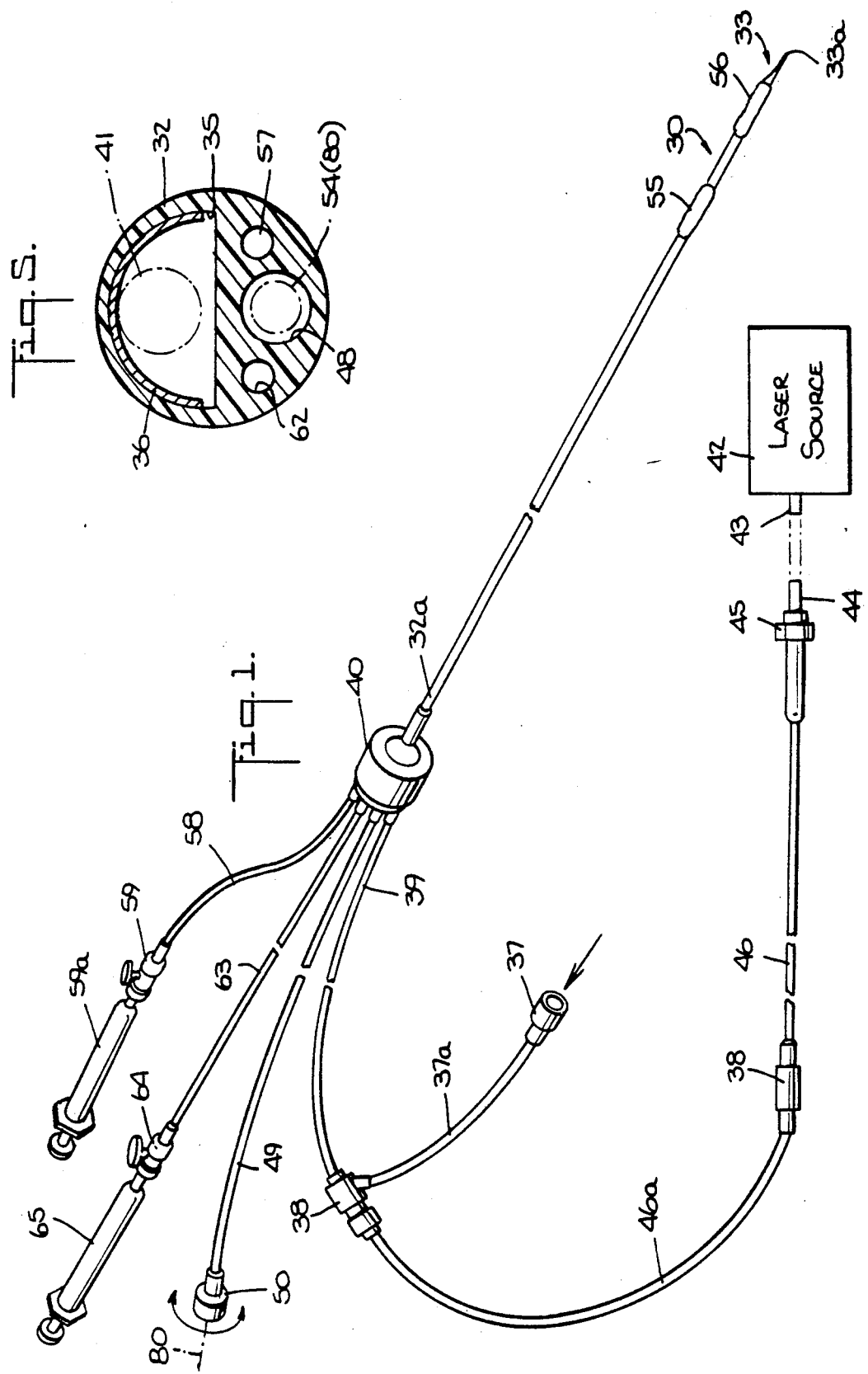

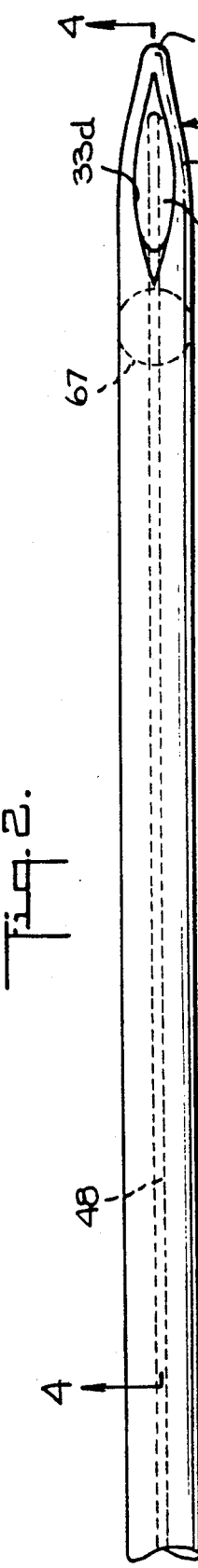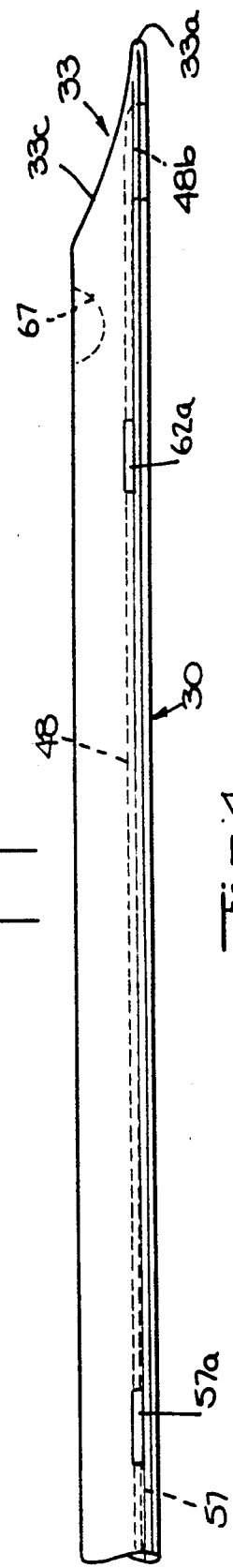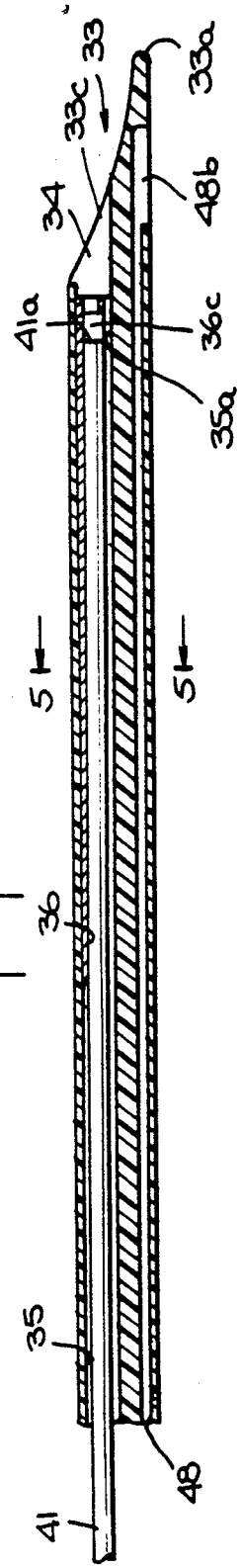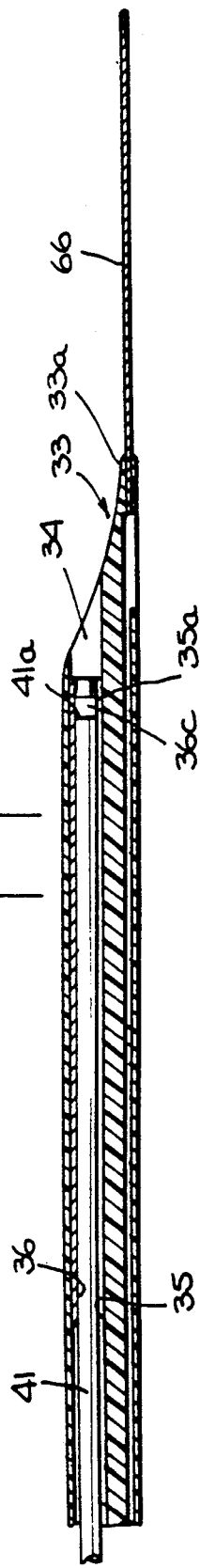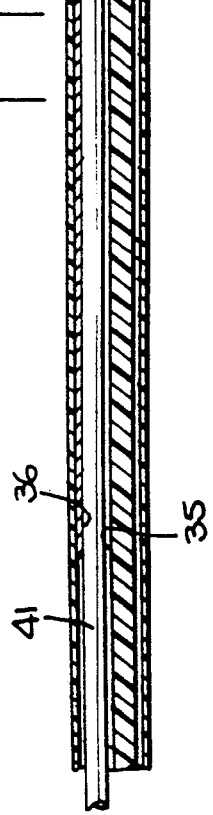

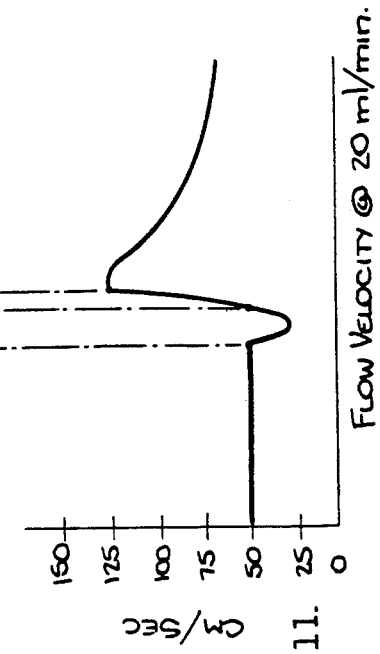
Fig. 10.
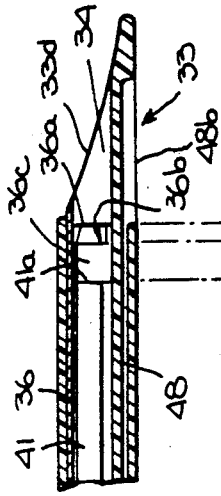
Fig. 11.
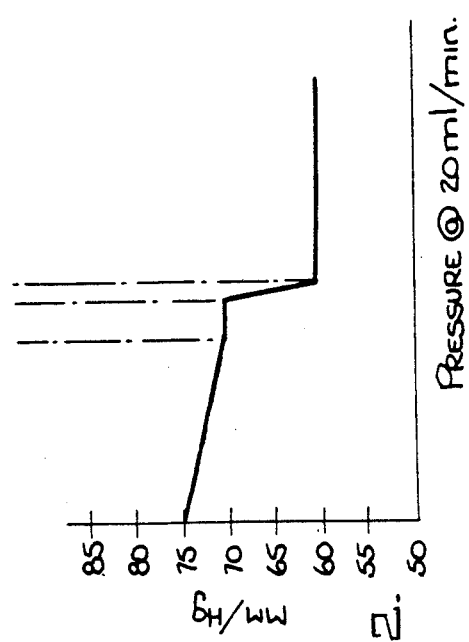
Fig. 12.
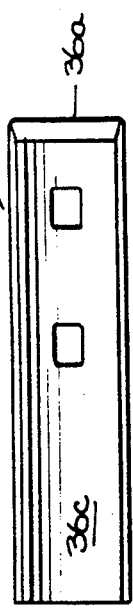
Fig. 7A.
Fig. 7B.
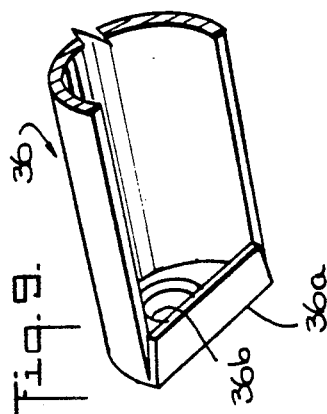
Fig. 9.
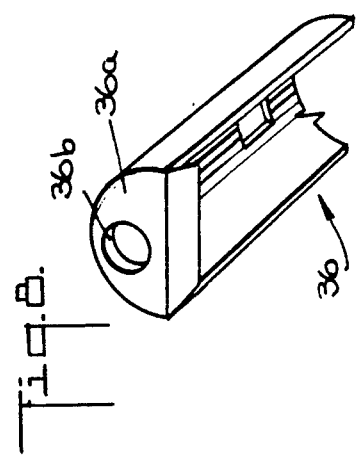
Fig. 8.

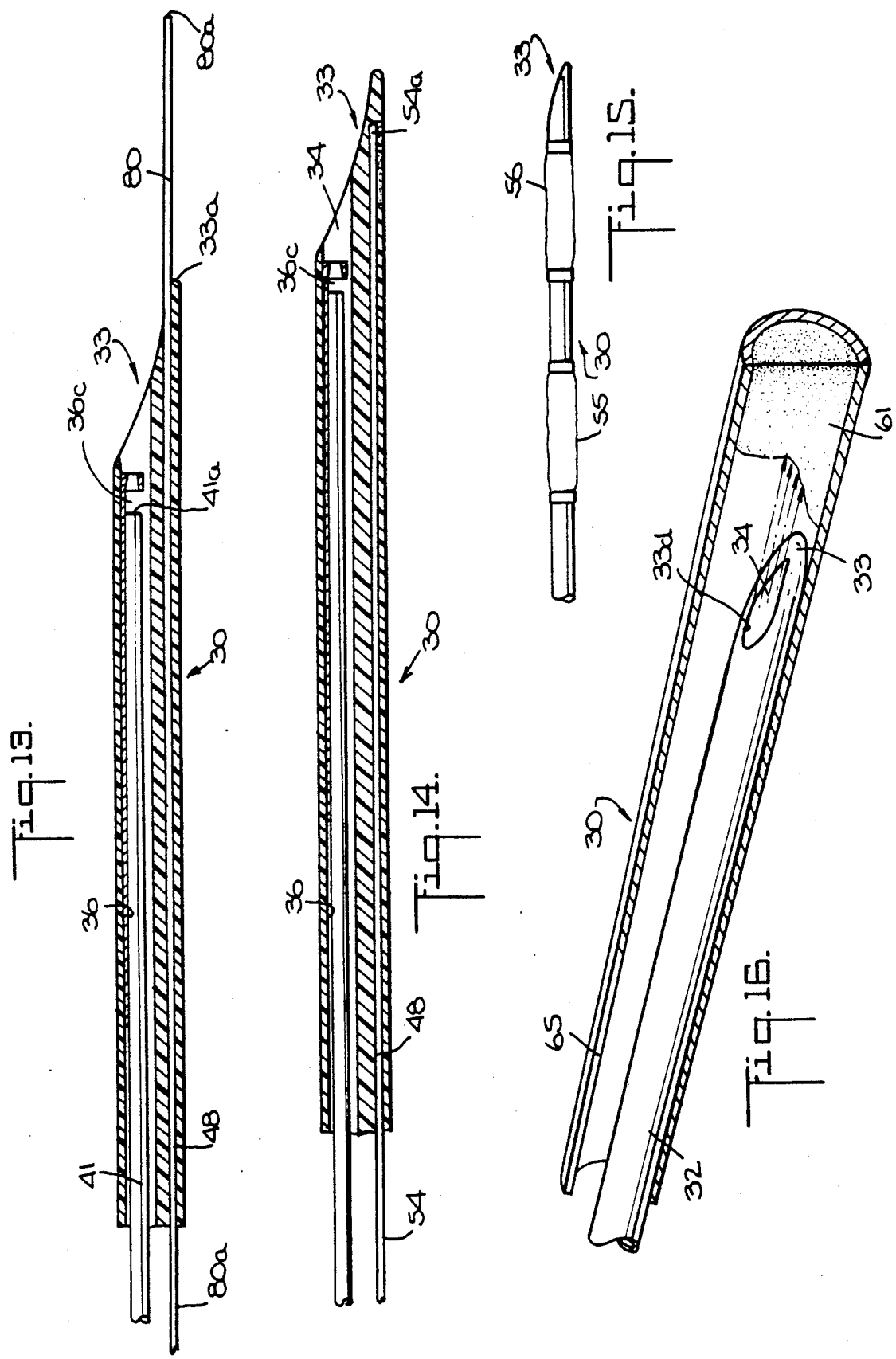

LASER ANGIOPLASTY CATHETER AND A METHOD FOR USE THEREOF

BACKGROUND OF THE INVENTION

This application is commonly owned with a related pending U.S. Patent Application, Ser. No. PCT/US 86/02617, filed Dec. 2, 1986, in the name of Michael E. Leckrone and entitled "ANGIOPLASTY CATHETER AND METHOD OF USE THEREOF".

1. Field of the Invention

The invention relates to laser angioplasty catheters which are adapted to be inserted into ducts within the body of a patient such as blood vessels including arteries and veins. The catheters of the invention are adapted to penetrate and disintegrate blockages, obstructions, occlusions, etc., or the like within the ducts in which the catheters are inserted. Thus, the catheters of the invention enable laser energy transmitted by an optical fiber or a bundle of optical fibers to be released from the distal end of the catheter to disintegrate or vaporize obstructions within blood vessels such as plaque in coronary, femoral, and other arteries. In use of an embodiment of the laser angioplasty catheters, the distal end of the catheter is positioned adjacent to the obstruction such as an occlusion or arteriosclerotic plaque which is to be removed from the duct. Due to the intense and concentrated energy level of the laser energy, such as pulsed laser energy, the laser angioplasty catheter of the invention must be adapted to prevent the laser energy from intersecting the internal wall of the duct at an angle or to a degree which could result in the possibility of damaging the duct. In addition, fluids within the duct such as blood within a blood vessel must be prevented from interfering with the transmission and release of the laser energy at the distal end of the catheter. It is also necessary to have control of the rotational position of the distal end of the catheter with respect to the duct in order that the catheter may operate upon an obstruction within a duct regardless of its circumferential position of the obstruction within the duct.

2. Description of the Prior Art

It is known in the prior art to provide a laser angioplasty catheter having a flexible shaft adapted to be inserted into a duct such as a blood vessel with a single or solid optical fiber or a bundle of optical fibers extending through the shaft to adjacent the distal end thereof. Laser energy such as pulsed laser energy is delivered to the proximal end of the optical fiber bundle and is emitted from the distal end thereof. When the laser energy intersects a blockage within the blood vessel, the laser energy disintegrates or vaporizes the blockage. By the application of suction to a lumen extending through the shaft, debris resulting from the disintegration or vaporization of the blockage can be withdrawn from the blood vessel U.S Pat. No. 4,627,436, issued Dec. 9, 1986, discloses a laser angioplasty catheter in which laser energy is delivered to a cavity or jaw formed by spaced abutments at the outer portion of the catheter adjacent to the distal end thereof. An inflatable balloon disposed opposite the abutments can be controllably inflated to urge the abutments toward the inner surface of the duct and thereby receive the blockage with the jaw between the abutments. Laser energy is emitted by the distal end portion of an optical fiber or fibers into the jaw in order to vaporize the blockage. The abutments adjacent to the distal end of the catheter prevent the laser energy from being propagated downstream of the distal end of the catheter and thereby prevent the laser energy from contacting the inner surface of the duct. A passage extending through the length of the catheter is adapted to apply suction to the jaw disposed between the abutments in order to remove debris therefrom. By rotating the catheter from the proximal end thereof, the distal end portion of the catheter can be rotated in order to position the abutments and the jaw therebetween within the circumference of the inner surface of the duct.

U.S. Pat. No. 4,685,458, issued Aug. 11, 1987, which is a division of U.S. Pat. No. 4,627,436, discloses a catheter similar to that of the 4,627,436 patent, but with an elongated element such as a cutting blade or a hot-wire extending between the abutments and adjacent to the jaw therebetween. The blade or hot-wire is adapted to cut or sever a blockage from the inner surface of the duct rather than to vaporize the obstruction by the application of laser energy.

U.S. Pat. No. 4,207,874, issued June 17, 1980, is another example of a laser angioplasty catheter. In this catheter, laser energy disintegrates or vaporizes an obstruction and suction is applied to a passage extending through the length of the catheter to withdraw debris produced by the application of the laser energy.

U.S. Pat. No. 4,573,470, issued Mar. 4, 1986, and U.S. Pat. No. 4,582,181, issued April 15, 1986, each disclose a steerable balloon dilation catheter in which the distal end of the tubular member of the catheter is bonded to the distal end of a core wire.

SUMMARY OF THE INVENTION

The invention of a laser angioplasty catheter device for disintegrating or vaporizing undesired material from a duct within the body of a patient comprises a catheter adapted to be disposed within the duct and having a snout-shaped distal end portion with a tip at one side thereof and a tapered surface extending from the tip toward the opposite side thereof. Means are provided adjacent to the distal end of the catheter for emitting laser energy from an opening in the tapered surface obstruction in the duct.

In another embodiment of the invention, means are provided for irrigating the distal end portion of the catheter adjacent to the obstruction being vaporized.

In still another embodiment of the invention, means are provided for removing debris of the obstruction being vaporized from adjacent the distal end portion of the catheter.

In an additional embodiment of the invention, the catheter is provided with a core wire extending through an internal passage within the catheter to adjacent the distal end portion thereof. At the distal end portion of the catheter, the core wire is secured to the catheter. With this arrangement, rotation of the proximal end of the core wire enables the distal end of the catheter to be rotated to position the snout-shaped distal end of the catheter circumferentially adjacent to the obstruction in the duct of the body of the patient.

In still a further embodiment of the invention, the optical fiber or fibers of the catheter device are extended through a lumen within the catheter adjacent the distal end portion of the catheter. The distal end of the lumen is provided with an orifice or nozzle which enables the velocity of a flow of an irrigating fluid delivered by the lumen to be controlled as it passes out of the orifice.

Therefore it is an object of the invention to provide a laser angioplasty catheter having a snout-shaped distal end portion with a tapered surface extending from the tip of the snout-shaped end portion for emitting pulsed laser energy from an opening in the tapered surface.

It is another object of the invention to provide a laser angioplasty catheter having a lumen for both delivering irrigating fluid to adjacent the distal end portion of the catheter and receiving the length of optical fiber therein.

It is an additional object of the invention to provide a laser angioplasty catheter in which there is provided a core wire extending through a lumen in the catheter and secured to the distal end portion thereof for rotation of the distal end portion in response to rotation of the proximal end portion of the core wire.

It is a further object of the invention to provide a laser angioplasty catheter in which the distal end portion of a lumen for delivering irrigation liquid is provided with means for controlling the flow dynamics of the liquid to prevent contact of blood or debris with the distal end portion of the optical fiber or fibers.

BRIEF DESCRIPTION OF THE DRAWINGS

FIG. 1 is a perspective view of an embodiment of the laser angioplasty catheter of the invention showing the snout-shaped distal end portion thereof and connections to the proximal end portion thereof;

FIG. 2 is a fragmentary plan view of an embodiment of the catheter of the invention having a snout-shaped distal end portion;

FIG. 3 is a fragmentary elevation view of the catheter of FIG. 2;

FIG. 4 is a fragmentary vertical section taken along line 4—4 in FIG. 2 and showing the optical fibers for directing laser energy through an opening in the snout-shaped distal end portion of the catheter and the arch support for supporting the shaft of the catheter;

FIG. 5 is vertical section taken along line 5—5 in FIG. 4 and showing a passage therein for irrigating fluid and the optical fibers and a lumen therein for aspiration;

FIG. 6 is a vertical section view showing another embodiment of the catheter device with a guide wire mounted adjacent to the tip of the snout-shaped distal end portion;

FIG. 7A is a fragmentary plan view showing an arch support for the distal end of the catheter with the end tab thereof in an intermediate position;

FIG. 7B is a fragmentary plan view showing the arch support for the distal end of the catheter with the end tab thereof in its final position;

FIG. 8 is a fragmentary perspective view of the exterior of the orifice at the distal end of the arch support;

FIG. 9 is a fragmentary perspective view of the orifice at the distal end of the arch support;

FIG. 10 is a fragmentary vertical section showing an orifice for directing irrigation liquid into the elongated opening at the distal end portion of the catheter;

FIG. 11 is a graphical representation of the flow velocity before, through and beyond the orifice of FIG. 10;

FIG. 12 is a graphical representation of the static pressure related to the velocities shown in FIG. 11;

FIG. 13 is a fragmentary vertical section showing a guidewire extending through the catheter;

FIG. 14 is a fragmentary vertical section showing the aspiration lumen of the catheter;

FIG. 15 is a fragmentary view of the catheter showing an occlusion balloon and a positioning balloon.

FIG. 16 is a fragmentary perspective view showing the snout-shaped distal end portion adjacent undesired material in a duct;

DESCRIPTION OF THE PREFERRED EMBODIMENTS

Figure 17:
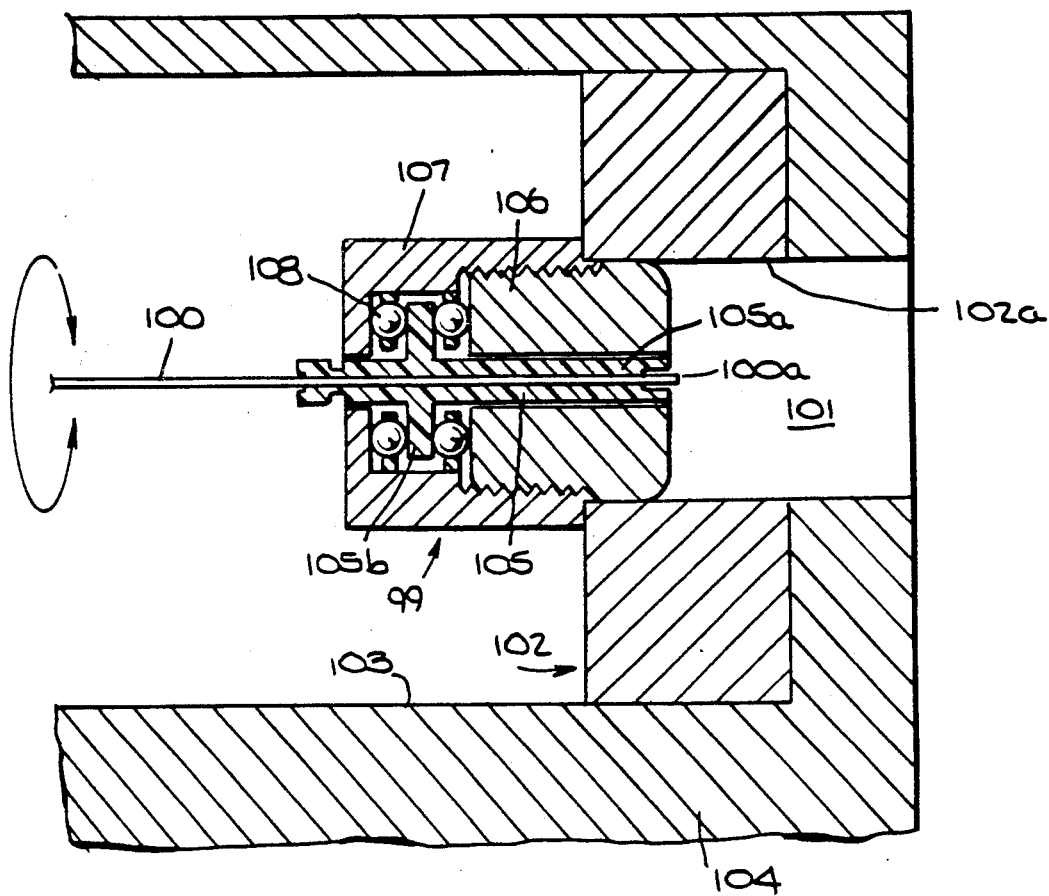
FIG. 17 is a fragmentary vertical section showing an embodiment of a rotatable connection of the optical fiber of the catheter device to a source of pulsed laser energy.

As shown in FIGS. 1, 2, 3, and 4, the laser angioplasty catheter 30 of the invention is adapted to be disposed within a duct in the body of a patient such as a blood vessel or an artery. The catheter shaft 32 has a snout-shaped end portion 33 which terminates in tip 33a. Snout-shaped end portion 33 comprises cylindrical surface 33b at one side and tapered or sloping surface 33c at the opposite side. Thus, the snout-shaped end portion enables the end portion to contact the wall of the blood vessel and then to be deflected toward the center of the interior of the blood vessel. Within the catheter shaft 32 there is disposed irrigation lumen 35 which extends to elongated opening 34 in communication with elliptically-shaped window 33d in tapered surface 33c. As shown in FIG. 1, irrigation liquid can be delivered to connector 37 and then through line 37a to junction 38. By means of coupling 40, the passage of line 39 is connected to irrigation lumen 35 and in this way, a flow of irrigation liquid such as saline can be delivered by irrigation lumen 35 to opening 34 and thereby to window 33d.

A fiber optic device such as single or solid optical fiber or a bundle of optical fibers, hereinafter collectively referred to as "optical fiber", e.g., optical fiber 41 extends from proximal end 32a (FIG. 1) of the catheter shaft 32 to the distal end 36a of arch support 36 (FIG. 6). Laser source 42 (FIG. 1) by means of coupling 43 is connected to optical fiber 44 which leads to rotary connector 45 which enables the optical fiber 46 to rotate freely with respect to the laser source. Optical fiber 46 extends from rotary connector 45 to junction 38. Beyond the junction 38, the optical fiber 46a extends through line 39 which is adapted to carry irrigation fluid from a supply (not shown) to which coupling 37 and line 37a are connected. Line 39 is connected to coupling 40. Within the coupling 40, optical fiber 41 enter passage 35 which extends to opening 34.

Aspiration lumen 48 which is shown by dash lines in FIGS. 2 and 3 and in FIG. 5 extends from proximal end portion 32a of the catheter shaft to adjacent elongated opening 34 where the aspiration passage is connected to aspiration notch 48b (FIGS. 2, 3 and 4) which is on the side of the catheter opposite elongated opening 34. The proximal end of aspiration lumen 48 within coupling 40 is connected to line 49 which in turn is coupled to knob 50. Knob 50 has a passage therethrough (not shown). Line 49 can be connected by the passage in knob 50 to a source 53 of negative pressure or suction (not shown). It therefore can be seen that upon the application of negative pressure to line 49, negative pressure is applied to aspiration lumen 48 and thereby to notch 48b. By means of notch 48b at opening 34, flow can be induced from the adjacent opening 34 and into the aspiration lumen 48. The aspiration lumen is optional. If an obstruction adjacent opening 34 is sufficiently disintegrated or vaporized by the laser pulses from the distal end of optical fiber 41, aspiration may not be required.

As shown in FIGS. 5 and 14, as an option, a core wire 54 can be extended through the aspiration lumen 48 if aspiration is not to be used. Distal end portion 54a of the core wire 54 (FIG. 14) is secured by bonding or like processes to snout-shaped end portion 33 of the catheter 30. In this arrangement core wire 54 extends to the proximal end portion 32a (FIG. 1) of catheter shaft 32, extends through coupling 40, and then through the interior of line 49 which provides negative pressure to aspiration passage 48. Further as shown in FIG. 1, core wire 54 can be extended outwardly from coupling 40 and through line 49 to operating knob 50. Rotation of knob 50 enables core wire 54 to be rotated. The core wire may be coated with materials such as fluorocarbon resin materials to reduce friction between the core wire and the aspiration passage when the core wire is rotated.

Rotation of core wire 54 by knob 50 in either of the directions shown by the arrows in FIG. 1 causes the core wire 54 to rotate freely within aspiration passage 48; however, since distal end portion 54a (FIG. 14) of the core wire is bonded or secured to snout-shaped end portion 33 of the catheter 32, the end portion 33 of the catheter is rotated in conjunction with rotation of the core wire 54. As a result, the snout-shaped end portion of catheter 33 can be rotated by the core wire 54 without rotating the remainder of shaft 32 of catheter device 30. The core wire may have a varying thickness with the greater thickness at the proximal end thereof. This provision minimizes "wind-up" in the core wire when it is rotated, increases flexibility at the distal end of the core wire, and reduces friction and thereby resistance to rotation of the core wire in the catheter.

In place of using core wire 54 to rotate the distal end portion 33 of the catheter, optical fiber 41 can be used by connecting the distal end 41a of the optical fiber to the distal end portion 33 of the catheter while the remainder of the optical fiber is free to rotate in its lumen. Thus upon rotating the proximal end 41b of the optical fiber, the distal end portion of the catheter can be rotated.

As shown in FIGS. 1 and 15, the distal end portion of catheter 30 can, as an option, be provided with occlusion balloon 55 and positioning balloon 56. Lumen 57 (FIGS. 3 and 5) which is in communication by port 57a (FIG. 3) with the occlusion balloon 55 as shown in FIGS. 1 and 15 extends through the catheter shaft 32, through coupling 40, to line 58, through valve 59 to a source of positive liquid (saline, for example) pressure such as syringe 59a. Thus, upon the introduction of positive pressure to passage 57, the occlusion balloon can be inflated, thereby sealing off the blood vessel and preventing the flow of blood about the distal end of the catheter. The level of blood pressure adjacent the snout-shaped distal end portion 33 of the catheter could cause a flow of blood along the catheter but for the blocking of the blood vessel by the occlusion balloon. Of course if the catheter of the invention is applied to arterial blood vessels 65 where the heart and such vessels have been temporarily bypassed by a blood pumping apparatus, then the occlusion balloon is unnecessary (FIG. 16).

Optional positioning balloon 56 as shown in FIGS. 1 and 15 is connected by port 62a (FIG. 3) to passage 62 (FIG. 5) which extends through the catheter shaft 32 to its proximal end portion 32a. Passage 62 is connected through coupling 40 to line 63 (FIG. 1) which is connected to valve 64 and in turn to a source of positive liquid pressure such as syringe 65. Upon directing catheter 30 to a position in which snout-shaped end portion 33 is adjacent to an obstruction and following the optional rotatable positioning of the distal end portion 33 by means of core wire 34, liquid pressure can be introduced into passage 62 in order to inflate positioning balloon 56. Since as shown in FIGS. 1 and 15, the positioning balloon 52 is disposed at a side of the snout-shaped distal end portion 33 of the catheter opposite to elongated opening 34, inflation of the positioning balloon 56 can urge the opening 34 to be moved toward the inner surface of the blood vessel, thereby bringing the occlusion adjacent to the opening 34 for application of pulsed laser energy thereto.

Guidewire 66 (FIG. 6) which can be a helix of fine filament material such as wire, as an option, can be mounted upon tip 33a of the catheter for the purpose of guiding the snout-shaped end portion 33 of the catheter within the blood vessel. Guiding of the catheter by tip 66 can be augmented by use of core wire 54 in rotating the snout-shaped distal end 33a of catheter 30 to enable the catheter to advance in a desired manner with respect to a blood vessel. Marker 67 (FIGS. 2 and 3) which can be formed from radio-opaque material such as platinum foil serves the function of enabling the location of the distal end of catheter 30 to be viewed by scanning means such as X-ray, fluoroscope, CAT scan, etc. In this way, the catheter 30 can be observed and controlled both with respect to its longitudinal position within the blood vessel as well as its rotatable position in placing the snout-shaped end portion adjacent to the obstruction.

As shown in FIG. 16, pulsed laser energy can be propagated from optical fiber 41 at its distal end portion 41a and through opening 34 and window 33d thereof to intersect and impinge upon an obstruction 61. Distal end portion 41a can be formed or contoured to provide a substantially collimated beam of pulsed laser energy, a convergent beam, or to an extent a divergent beam.

As shown by a dash line 80 in FIG. 1, catheter 30 can be provided with guidewire 80 which extends freely through a passage in knob 50, through line 49, and through a lumen extending through tip 33a. By way of example, guidewire 80 can be extended through aspiration lumen 48 (FIG. 13). In use, the guidewire 80 is threaded through the blood vessel under the control of a scanning device external to the body of the patient such as X-ray, CAT scan, etc. until the distal end portion 80a of the guidewire is disposed in the desired blood vessel and adjacent the obstruction which is to be removed. Thereafter, the proximal end of the guidewire is threaded through a passage (not shown) in tip 33a of the snout-shaped end portion of catheter 30. The catheter is then advanced along the guidewire 80 and through the blood vessel with the path of travel of the tip 33a of the catheter being guided b the location of the guidewire. The guidewire 80 can be disposed, as an option, in aspiration passage 48 (not shown) connecting passage tip 33a of the catheter to aspiration passage 48.

In FIGS. 4, 7A, 7B, 8 and 9, there is shown arch support 36. As shown in FIG. 4, arch support 36 is disposed within the distal end 35a of lumen 35 through which optical fiber 41 extends. As shown in FIGS. 7A, 7B, 8 and 9, arch support 36 is a semicylindrically-shaped metal shield which has an orifice or nozzle 36b in end wall 36a. The metal arch support is disposed within distal end portion of the irrigation lumen 35. The end wall portion 36a of the metal arch support which is provided with orifice 36b faces and is in communication with opening 34.

As shown in FIG. 4, the distal end portion 41a of optical fiber 41 terminates at a distance 36c from the end wall portion 36a of the metal arch support. As shown in the graph of FIG. 11, the flow velocity decreases in distance 36c. Further as shown, the velocity increases to a maximum within the orifice 36b. Orifice 36b is disposed in facing relationship with distal end portion 41a of the optical fiber and adjacent opening 34. The orifice forms a window through which laser energy is transmitted to opening 34. Optical fiber 41 is supported at its distal end portion adjacent to metal arch support 36 by being bonded or cemented to the inner surface 36c of the arch support.

In use, catheter 30 is positioned within a blood vessel 65 until the snout-shaped end portion 33 is positioned adjacent to an obstruction or the like in the blood vessel (FIG. 16). Thereafter, the flow irrigation liquid is controlled by orifice or nozzle 36b in being delivered to opening 34. The pulsed laser energy passing through opening 34 disintegrates or vaporizes the obstruction 61 adjacent thereto. The metal arch support 36 protects the distal end portion of the catheter during the application of the laser energy to the obstruction. In addition the metal arch support 36 prevents collapse of the lumen 35 whenever balloon 56 is inflated.

In FIGS. 8, 9 and 10, there is shown the orifice 36b of arch support 36. Optical fiber 41 is disposed in the arch support. During the delivery of pulsed laser energy by optical fiber 41, irrigation fluid is transmitted through lumen 35 and into the distance 36b in advance of orifice 36b (FIGS. 13 and 14).

The curve identified as "Flow Velocity" in FIG. 11, shows the relative velocity of the irrigation fluid within lumen 35, distance 36c and orifice 36b. It can be seen that upon the fluid flow entering the cross section of the distance 36c which is substantially larger than the cross section of passage 35, the flow velocity is reduced. Thereafter, as the flow passes through nozzle 36b, the flow velocity increases and reaches a maximum. This arrangement ensures that blood or the debris from an obstruction being disintegrated adjacent opening 34 cannot enter the nozzle 36b or distance 36c and thereby cannot come into contact with the distal end 41a of the optical fiber. In this way, the possibility of blood or debris contacting the distal end 41a of the optical fiber and damaging or destroying the optical fiber is eliminated.

The curve in FIG. 12 marked "Pressure" shows the relative pressure level of the irrigating fluid in the distal end portion of lumen 35a, in distance 36c, and in orifice 36b. Further as shown in FIG. 10, the orifice 36b serves as an aperture for the laser energy being transmitted toward opening 34. Thus, the orifice can act as a stop or diaphragm to limit the size of the beam of laser energy being delivered to opening 34.

FIG. 17 shows a rotational connector 99 for a bundle of optical fibers 100 which, by way of example may have a diameter of 1,000 microns. Test experience has shown that where a single fiber or a bundle of optical fibers are used, the stiffness of the bundle of optical fibers 100 may prevent the catheter devices as hereinabove described from being rotated about the bundle of optical fibers. The rotational connector enable rotation of the optical fiber bundle and thereby enables the catheter to be rotated. Another requirement of the rotational connector is that it must be capable of aligning the optical fibers 100 and a laser beam (not shown) directed from a source of laser energy through cavity 101 toward the proximal end portion 100a of the optical fibers.

Positioner 102 is adapted to be mounted with recess 03 of the outer housing 104 of a source of laser energy (not shown). Optical fibers 100 are fixedly mounted with respect to ferrule 105. The ferrule includes shaft portion 105a and disc portion 105b. Carrier 106 is threadedly mounted within socket 107. The carrier is mounted within bore 102a of positioner 102. The positioner is adapted to be translated in orthogonal directions in a plane at right angles to the axis of the optical fibers 100 as shown in FIG. 17 in order to align the distal end portion 100a thereof with the laser beam propagated into cavity 101 by the source of laser energy. Ferrule 105 is rotatably mounted in carrier 106, thereby enabling the optical fibers to be rotated with respect to the source of laser energy. To position the optical fibers along their longitudinal axis with respect to the source of laser energy, disc 105b is maintained at a predetermined position with respect to cavity 101 by thrust bearings 108 mounted in socket 107 which can comprise ball bearings 108 in contact with each of the oppositely disposed outer surfaces of disc 105b. The result is that the ferrule 105 is free to rotate and yet cannot be translated with respect to the source of laser energy.

Figure 18:
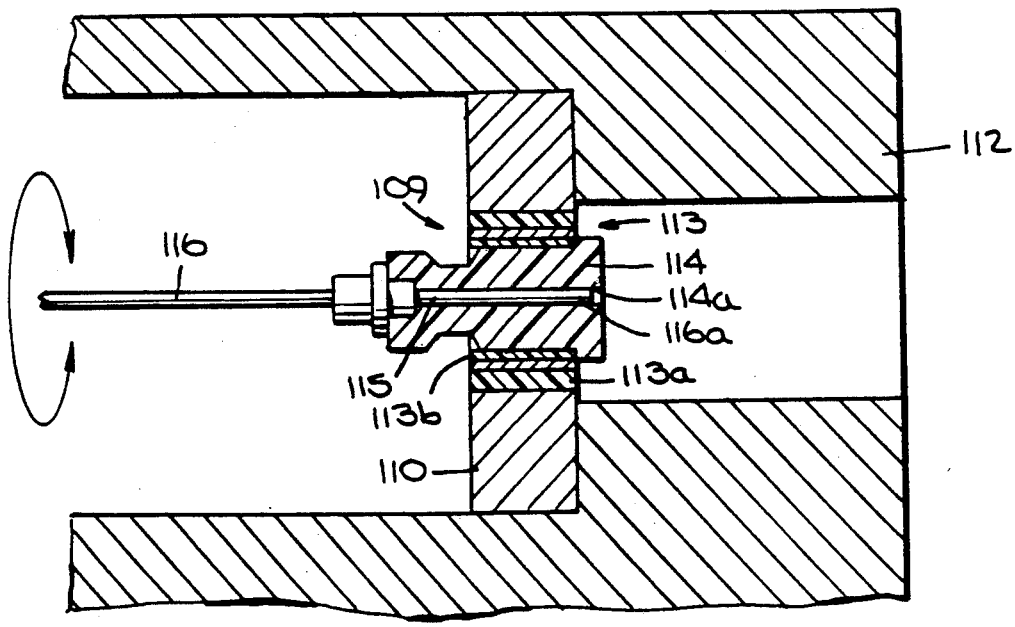
FIG. 18 is a fragmentary vertical section of another embodiment of a rotatable connection of the optical fiber to a source of pulsed laser energy.

Another embodiment of a rotatable connector is shown in FIG. 18, namely connector 109. As in the embodiment of FIG. 17, positioner 110 is adapted to be adjustably mounted within recess 111 of housing 112 of the laser source (not shown). Bearing 113 is a precision roller or needle bearing having outer race 113a and inner race 113b. Socket 114 is pressed into inner race 113b. Sleeve 115 through which optical fiber socket 114. As a result of this arrangement, precision bearing 113 can control the position of the proximal end 116a of the optical fibers in both a direction radial to the longitudinal axis of the fibers and in the direction of the longitudinal axis.

What is claimed is:

1. A laser angioplasty catheter device comprising a catheter having a distal end portion adapted to be inserted within a duct in the body of a patient and a proximal end portion, the distal end portion comprising a tip disposed at one side of the catheter, the distal end portion having a tapered surface extending from the tip to the side of the catheter opposite the one side, the catheter having a lumen extending through the length thereof and having a distal end portion intersecting the tapered surface extending from the tip of the catheter, the intersection of the lumen and the distal end portion forming an elongated opening extending along the length of the tapered surface, an optical fiber extending within the interior of the lumen from the proximal end thereof to adjacent and spaced apart from the distal end portion of the lumen, the optical fiber being adapted to be connected to a source of laser energy, an elongated annular element disposed adjacent the distal end of the lumen and the distal end of the optical fiber, the annular element having an opening therein for transmitting laser energy from the optical fiber toward the elongated opening in the tapered surface to deliver said laser energy through the elongated opening into the duct, and further comprising a cylindrical shield attached to the annular element and extending away from the distal end of the lumen with the longitudinal axis of the cylindrical shield being substantially parallel to the longitudinal axis of the lumen, the shield being formed of material for absorbing laser energy which does not pass through the opening in the annular element to protect the interior surface of the distal end portion of the lumen.

2. A catheter device in accordance with claim 1 in which the cylindrical shield is formed of metal material.

3. A catheter device in accordance with claim 1 in which the cylindrical shield is substantially semicircular in cross-section.

4. A laser angioplasty catheter device comprising a catheter having a distal end portion adapted to be inserted within a duct in the body of a patient and a proximal end portion, the distal end portion comprising a tip disposed at one side of the catheter, the distal end portion having a tapered surface extending from the tip to the side of the catheter opposite the one side, the catheter having a lumen extending through the length thereof and having a distal end portion intersecting the tapered surface extending from the tip of the catheter, the intersection of the lumen and the distal end portion forming an elongated opening extending along the length of the tapered surface, an optical fiber extending within the interior of the lumen from the proximal end thereof to adjacent and spaced apart from the distal end portion of the lumen, the optical fiber being adapted to be connected to a source of laser energy to deliver laser energy through the elongated opening into the duct, and further comprising an additional lumen extending throughout the length of the catheter, and a filament extending along the length of the additional lumen to adjacent the distal end of the catheter and movable with respect to the lumen, the filament being connected to the distal end portion of the catheter, the distal end portion of the catheter being adapted to be rotated in response to rotation of the filament, whereby the distal end portion of the catheter is adapted to be positioned and rotated by the filament within the duct, and in which the filament has a varying thickness throughout its length with the maximum thickness thereof being adjacent the proximal end portion of the catheter and the minimum thickness thereof being connected to the distal end portion of the catheter.

5. A laser angioplasty catheter device comprising a catheter having a distal end portion adapted to be inserted within a duct in the body of a patient and a proximal end portion, the distal end portion comprising a tip disposed at one side of the catheter, the distal end portion having a tapered surface extending from the tip to the side of the catheter opposite the one side, the catheter having a lumen extending through the length thereof and having a distal end portion intersecting the tapered surface extending from the tip of the catheter, the intersection of the lumen and the distal end portion forming an elongated opening extending along the length of the tapered surface, an optical fiber extending within the interior of the lumen from the proximal end thereof to adjacent and spaced apart from the distal end portion of the lumen to deliver laser energy through the elongated opening into the duct, an additional lumen extending throughout the length thereof, and a filament extending along the length of the additional lumen to adjacent the distal end of the catheter and movable with respect to the lumen, the filament being connected to the distal end portion of the catheter, the distal end portion of the catheter being adapted to be rotated in response to rotation of the filament, the filament having a varying thickness throughout its length with the maximum thickness thereof being adjacent the proximal end portion of the catheter and the minimum thickness thereof being connected with the distal end portion of the catheter, whereby the distal end portion of the catheter is adapted to be positioned and rotated by the filament within the duct.

6. A catheter device in accordance with claim 5 in which the filament contains an outer surface conditioned to reduce friction between the filament and the lumen in which it is disposed.

7. A catheter device in accordance with claim 5 in which the outer surface of the filament conditioned to reduce friction comprises a coating of a low surface friction resin material.

8. A catheter device in accordance with claim 7 in which the low surface friction resin material comprises a fluorocarbon resin material.

9. A catheter device in accordance with claim 5 in which the lumen through which the length of the filament extends is an aspiration lumen.

10. A laser angioplasty catheter device comprising a catheter having a distal end portion adapted to be inserted within a duct in the body of a patient and a proximal end portion, the distal end portion comprising a tip disposed at one side of the catheter, the distal end portion having a tapered surface extending from the tip to the side of the catheter opposite the one side, the catheter having a lumen extending through the length thereof and having a distal end portion intersecting the tapered surface extending from the tip of the catheter, the intersection of the lumen and the distal end portion forming an elongated opening extending along the length of the tapered surface, an optical fiber extending within the interior of the lumen from the proximal end thereof to adjacent the spaced apart from the distal end portion of the lumen, the optical fiber being adapted to be connected to a source of laser energy to deliver laser energy through the elongated opening into the duct, an irrigation lumen for delivering irrigation liquid to adjacent the elongated opening, and a nozzle having a converging opening therein that connects the irrigation lumen to the elongated opening to increase the velocity of irrigation liquid passing through the nozzle lumen as the irrigation liquid enters adjacent the elongated opening, the opening of the nozzle transmitting the laser energy from the distal end portion of the optical fiber to the elongated opening.

11. A method for removing undesired material from a duct within a patient's body by use of a catheter having a proximal end portion and a distal end portion, said distal end portion adapted to be inserted within a duct in the patient's body, the catheter having means disposed adjacent the distal end portion of the catheter for intersecting and releasing undesired material from the interior of the blood vessel when the distal end portion of the catheter is disposed adjacent to the undesired material, an inflatable bladder mounted on the catheter adjacent the distal end portion thereof; the catheter further including an irrigation lumen extending through the length of the catheter for passing a flow of irrigation liquid to the distal end portion of the catheter, an optical fiber extending within the interior of the catheter from the proximal end thereof to the distal end of the catheter to deliver pulsed laser energy to the undesired material and; a filament extending along the length of the catheter to adjacent the distal end of the catheter, the catheter being rotatably disposed about the filament and adapted to be rotated with respect to the filament; the method comprising the steps of:
 delivering the irrigation liquid from the distal end of the catheter toward the undesired material adjacent the distal end of the optical fiber;
 placing the distal end portion of the catheter adjacent the undesired material;
 applying laser energy to the undesired material to release the material from blood vessel; and
 rotating and positioning the distal end portion of the catheter with respect to the undesired material by rotating the filament.

12. A laser angioplasty catheter device comprising a catheter having a distal end portion adapted to be inserted within a duct in the body of a patient and a proximal end portion,
 the distal end portion comprising a tip disposed at one side of the catheter, the distal end portion having a tapered surface extending from the tip to the side of the catheter opposite the one side,
 the catheter having a lumen extending through the length thereof and having a distal end portion intersecting the tapered surface extending from the tip of the catheter, the intersection of the lumen and the distal end portion forming an elongated opening extending along the length of the tapered surface,
 an optical fiber extending within the interior of the lumen from the proximal end thereof to adjacent and spaced apart from the distal end portion of the lumen to deliver laser energy through the elongated opening in the duct,
 an elongated annular element disposed adjacent the distal end of the lumen and the distal end of the optical fiber, the annular element having an opening therein for transmitting laser energy from the optical fiber toward the elongated opening in the tapered surface, and
 a cylindrical shield attached to the annular element and extending away from the distal end of the lumen with the longitudinal axis of the cylindrical shield being substantially parallel to the longitudinal axis of the lumen, the shield being formed of material for absorbing laser energy which does not pass through the opening in the annular element to protect the interior surface of the distal end portion of the lumen;
 whereby the laser energy is adapted to cause excision of undesired material within the duct when the distal end portion of the catheter is disposed adjacent to the undesired material and the optical fiber is connected to a source of laser energy.

13. A laser angioplasty catheter device comprising a catheter having a distal end portion adapted to be inserted within a duct in the body of a patient and a proximal end portion,
 the distal end portion comprising a tip disposed at one side of the catheter, the distal end portion having a tapered surface extending from the tip to the side of the catheter opposite the one side,
 the catheter having a lumen extending through the length thereof and having a distal end portion intersecting the tapered surface extending from the tip of the catheter, the intersection of the lumen and the distal end portion forming an elongated opening extending along the length of the tapered surface,
 an optical fiber extending within the interior of the lumen from the proximal end thereof to adjacent and spaced apart from the distal end portion of the lumen to deliver laser energy through the elongated opening into the duct,
 the catheter including an irrigation lumen for delivering irrigation liquid to adjacent the elongated opening, and
 a nozzle having a converging opening therein connecting the irrigation lumen to the elongated opening to increase the velocity of irrigation liquid passing through the nozzle lumen as the irrigation liquid enters adjacent the elongated opening, the opening of the nozzle transmitting the laser energy from the distal end portion of the optical fiber to the elongated opening,
 whereby laser energy is adapted to cause excision of undesired material within the duct when the distal end portion of the catheter is disposed adjacent to the undesired material and the optical fiber is connected to a source of laser energy.

14. A catheter device in accordance with claim 13 in which the distal end portion of the optical fiber is spaced apart from the nozzle within the irrigation lumen to form a transition passage for the irrigation liquid in advance of its entry into the nozzle.

15. A laser angioplasty catheter device comprising a catheter having a distal end portion adapted to be inserted within a duct in the body of a patient and a proximal end portion,
 the distal end portion comprising a tip disposed at one side of the catheter, the distal end portion having a tapered surface extending from the tip to the side of the catheter opposite the one side,
 the catheter having a lumen extending through the length thereof and having a distal end potion intersecting the tapered surface extending from the tip of the catheter, the intersection of the lumen and the distal end portion forming an elongated opening extending along the length of the tapered surface, and
 an optical fiber extending within the interior of the lumen from the proximal end thereof to adjacent and spaced apart from the distal end portion of the lumen to deliver laser energy through the elongated opening in the duct, the optical fiber being movable with respect to the lumen, and means connecting the optical fiber to the distal end portion of the catheter, the distal end portion of the catheter being adapted to be rotated in response to rotation of the proximal end of the optical fiber, whereby the distal end portion of the catheter is adapted to be positioned and rotated by the optical fiber within the duct to enable the laser energy to cause excision of undesired material within the duct when the distal end portion of the catheter is disposed adjacent to the undesired material and the optical fiber is connected to a source of laser energy.

* * * * *